(12) United States Patent
Park et al.

(10) Patent No.: US 8,367,060 B2
(45) Date of Patent: Feb. 5, 2013

(54) PHARMACEUTICAL COMPOSITION CONTAINING ARAZYME FOR THE PREVENTION OF LIVER DYSFUNCTION

(75) Inventors: Ho-Yong Park, Daejeon (KR); Kwang-Hee Son, Daejeon (KR); Dong-Ha Shin, Daejeon (KR); Kyu-Shik Jeong, Daegu (KR)

(73) Assignee: Insect Biotech Co., Ltd., Daejeon (KR)

( * ) Notice: Subject to any disclaimer, the term of this patent is extended or adjusted under 35 U.S.C. 154(b) by 0 days.

(21) Appl. No.: 13/234,847

(22) Filed: Sep. 16, 2011

(65) Prior Publication Data

US 2012/0003205 A1    Jan. 5, 2012

Related U.S. Application Data

(62) Division of application No. 12/521,618, filed as application No. PCT/KR2006/005835 on Dec. 28, 2006.

(51) Int. Cl.
*A61K 38/48* (2006.01)
(52) U.S. Cl. .............. 424/94.63; 424/94; 424/96.63; 514/12; 514/2
(58) Field of Classification Search .............. None
See application file for complete search history.

(56) References Cited

U.S. PATENT DOCUMENTS

| 7,247,467 | B2 * | 7/2007 | Cheng et al. | 435/252.3 |
| 2008/0207646 | A1 * | 8/2008 | Choi et al. | 514/262.1 |
| 2009/0317374 | A1 * | 12/2009 | Park et al. | 424/94.63 |

FOREIGN PATENT DOCUMENTS

| KR | 10-1998-69206 A | 10/1998 |
| KR | 10-2001-112928 A | 12/2001 |
| WO | WO 01/57222 | 8/2001 |

OTHER PUBLICATIONS

Bersanetti, et al., Characterization of arazyme, an exocellular metalloprotease isolated from *Serratia proteamaculans* culture medium, Enzyme and Microbial Technology, 2005, 37(6):574-581.
Oster Sessuib Abstracts, Bio International Convention, Jun. 17-20, 2008.
Park, et al., Hepatoprotective effect of Arazyme on CCl4-induced acute hepatic injury in SMP30 knock-out mice, Toxicology, 2008, 246(2-3):132-142.
Wells, Biochemistry, vol. 29, pp. 8509-8717, 1990.
Seffernick, et al., J. Bacteriology, vol. 183, pp. 2405-2410, 2010.
International Search Report mailed Sep. 21, 2007 issued for corresponding PCT International Application No. PCT/KR2006/005835.

* cited by examiner

*Primary Examiner* — Hope Robinson
(74) *Attorney, Agent, or Firm* — Lucas & Mercanti, LLP

(57) ABSTRACT

The present invention relates to a composition and a method for the treatment of liver dysfunction which contains administration of a composition containing arazyme as an active ingredient, more precisely arazyme produced by *Aranicola proteolyticus*. The arazyme of the present invention inhibits apoptosis in injured liver cells, increases SMP30 expression, inhibits P-smad3 expression and protects the liver by inhibiting liver injury around the central vein region. Therefore, the arazyme of the invention can be effectively used as a composition for the treatment of liver dysfunction.

7 Claims, 15 Drawing Sheets

SEQUENCE LISTING

```
<160> NUMBER OF SEQ ID NOS: 2

<210> SEQ ID NO 1
<211> LENGTH: 487
<212> TYPE: PRT
<213> ORGANISM: Aranicola proteolyticus
```

-continued

```
<220> FEATURE:
<221> NAME/KEY: BINDING
<222> LOCATION: (192)..(192)
<223> OTHER INFORMATION: Zn binding site
<220> FEATURE:
<221> NAME/KEY: BINDING
<222> LOCATION: (196)..(196)
<223> OTHER INFORMATION: Zn binding site
<220> FEATURE:
<221> NAME/KEY: BINDING
<222> LOCATION: (323)..(323)
<223> OTHER INFORMATION: Zn binding site

<400> SEQUENCE: 1

Met Gln Ser Thr Lys Lys Ala Ile Glu Ile Thr Glu Ser Ser Leu Ala
1               5                   10                  15

Ala Ala Ser Ser Ala Tyr Asn Ala Val Asp Asp Leu Leu His Tyr His
            20                  25                  30

Glu Arg Gly Asn Gly Ile Gln Val Asn Gly Lys Asp Ser Phe Ser Thr
        35                  40                  45

Glu Gln Ala Gly Leu Phe Ile Thr Arg Glu Asn Gln Thr Trp Asn Gly
    50                  55                  60

Tyr Lys Val Phe Gly Gln Pro Val Lys Leu Thr Phe Ser Phe Pro Asp
65                  70                  75                  80

Tyr Lys Phe Ser Ser Thr Asn Val Ala Gly Asp Thr Gly Leu Ser Lys
                85                  90                  95

Phe Ser Ala Glu Gln Gln Gln Ala Lys Leu Ser Leu Gln Ser Trp
            100                 105                 110

Ser Asp Val Ala Asn Ile Thr Phe Thr Glu Val Gly Ala Gly Gln Lys
            115                 120                 125

Ala Asn Ile Thr Phe Gly Asn Tyr Ser Gln Asp Arg Pro Gly His Tyr
        130                 135                 140

Asp Tyr Asp Thr Gln Ala Tyr Ala Phe Leu Pro Asn Thr Ile Tyr Gln
145                 150                 155                 160

Gly Gln Asn Leu Gly Gly Gln Thr Trp Tyr Asn Val Asn Gln Ser Asn
                165                 170                 175

Val Lys His Pro Ala Ser Glu Asp Tyr Gly Arg Gln Thr Phe Thr His
            180                 185                 190

Glu Ile Gly His Ala Leu Gly Leu Ser His Pro Gly Asp Tyr Asn Ala
        195                 200                 205

Gly Glu Gly Asn Pro Thr Tyr Arg Asp Ala Ser Tyr Ala Glu Asp Thr
    210                 215                 220

Arg Glu Phe Ser Leu Met Ser Tyr Trp Ser Glu Thr Asn Thr Gly Gly
225                 230                 235                 240

Asp Asn Gly Gly His Tyr Ala Ala Ala Pro Leu Leu Asp Asp Ile Ser
                245                 250                 255

Ala Ile Gln His Leu Tyr Gly Ala Asn Gln Thr Thr Arg Thr Gly Asp
            260                 265                 270

Thr Val Tyr Gly Phe Asn Ser Asn Thr Gly Arg Asp Phe Leu Ser Thr
        275                 280                 285

Thr Ser Asn Pro Gln Lys Val Ile Phe Ala Ala Trp Asp Ala Gly Gly
    290                 295                 300

Asn Asp Thr Phe Asp Phe Ser Gly Tyr Thr Ala Asn Gln Arg Ile Asn
305                 310                 315                 320

Leu Asn Glu Lys Ser Phe Ser Asp Val Gly Gly Leu Lys Gly Asn Val
                325                 330                 335

Ser Ile Ala Ala Gly Val Thr Ile Glu Asn Ala Ile Gly Gly Ser Gly
            340                 345                 350
```

```
Asn Asp Val Ile Val Gly Asn Ala Ala Asn Asn Val Leu Lys Gly Gly
            355                 360                 365

Ala Gly Asn Asp Val Leu Phe Gly Gly Gly Ala Asp Glu Leu Trp
370                 375                 380

Gly Gly Ala Gly Lys Asp Thr Phe Val Phe Ser Ala Val Ser Asp Ser
385                 390                 395                 400

Ala Pro Gly Ala Ser Asp Trp Ile Lys Asp Phe Gln Lys Gly Ile Asp
                405                 410                 415

Lys Ile Asp Leu Ser Phe Phe Asn Gln Gly Ala Gln Gly Gly Asp Gln
                420                 425                 430

Ile His Phe Val Asp His Phe Ser Gly Ala Ala Gly Glu Ala Leu Leu
            435                 440                 445

Ser Tyr Asn Ala Ser Asn Asn Val Ser Asp Leu Ala Leu Asn Ile Gly
            450                 455                 460

Gly His Gln Ala Pro Asp Ile Leu Val Lys Ile Val Gly Gln Val Asp
465                 470                 475                 480

Val Ala Thr Asp Phe Ile Val
            485

<210> SEQ ID NO 2
<211> LENGTH: 2481
<212> TYPE: DNA
<213> ORGANISM: Aranicola proteolyticus
<220> FEATURE:
<221> NAME/KEY: misc_feature
<222> LOCATION: (402)..(402)
<223> OTHER INFORMATION: n is a, c, g, or t

<400> SEQUENCE: 2
cgagcgcgaa agacccggaa ggcacgaggt gattagtcaa aaaagaaaaa tgttattcct      60
gcgggaacta aaaagtaccg gcggctaata ataaagagtt attaatctat aacgctttag     120
ccaaatttaa cttttagccg tctaaatccc agcacgattc gcttggctct gcaggccgca     180
tttttgttgg agtttgttac caactcatgg catttaagtt tcattaatat tgtaaataat     240
gcaaaaaacc agcataaatc cccttcgtaa cgataataaa tggctgatta ttttatgtgc     300
agttttacac cgctgcctat aattggaatc gattaccatt tatggtggta atcttatttg     360
ctgatatata tgcattaatt ctctctaaca cactgccggt ancggcgcat aaactccttc     420
ccgtaagcgt gcggttcgtt ctccgtggct tcctggcagg ttatgtctat ctgtctgatt     480
gaaaccaatc agctaatgag tggaatcgaa ccaatgcaat ctactaaaaa ggcaattgaa     540
attactgaat ccagccttgc ggctgcgagc tccgcttaca atgcagtaga tgatttgctg     600
cattatcatg agcgaggcaa cgggattcag gttaatggca aggactcatt ttctaccgaa     660
caagccgggc tgtttattac ccgcgagaac caaacctgga acggttataa agttttggc      720 caaccggtta aattaacgtt ctctttcccg gattataaat tctcttccac caacgtcgcc     780
ggcgataccg gactgagcaa attcagcgcg aacagcagc agcaggctaa gctgtcgctg      840
cagtcctggt ctgacgtggc caatatcacc tttaccgaag ttggtgccgg ccagaaggcc     900
aatatcacct tcggtaacta cagccaggat cgtcccggcc attatgacta cgatacccag     960
gcttacgcct cctgccgaa caccatttat cagggccaaa acctgggcgg gcagacttgg    1020
tacaacgtca accagtccaa cgtgaaacat ccggccagcg aagactacgg ccgccagacc    1080
tttacccacg agattggcca tgcgttgggc ttgagccatc cgggcgatta aacgccggc     1140 gaaggcaacc cgacttacag agatgccagc tacgccgaag atactcgtga gttcagcctg    1200
```

```
atgagttact ggagcgaaac caacaccggt ggcgacaacg gcgggcacta cgctgcggcg    1260
ccactgctgg atgacatttc cgctattcag catctgtatg gtgccaacca gaccacccgt    1320
accggcgata ccgtgtatgg cttcaactca aataccggac gtgacttcct cagtaccacc    1380
agcaatccgc aaaaagtgat ctttgcggcc tgggatgcgg gtggtaatga caccttcgat    1440
ttctccggtt acaccgctaa ccagcgtatt aatctgaacg agaaatcttt ctccgacgtg    1500
ggtgggctga aaggcaacgt gtccattgcc gcaggtgtga ccatcgagaa cgcgattggc    1560
ggttcaggca atgacgtgat cgtcggcaat gcggccaaca acgtgctgaa aggtggcgcg    1620
ggcaacgacg tgctgttcgg cggtggtggg gctgatgagc tgtggggcgg tgcgggcaaa    1680
gacacctttg tcttctctgc ggtcagcgat tctgcgccgg gtgcctccga ctggatcaag    1740
gatttccaga aaggcatcga taaaatcgac ctgtcattct tcaatcaggg cgcgcagggt    1800
ggcgatcaga tccacttcgt cgatcatttc agtggcgcag cgggcgaagc cttgctgtct    1860
tacaatgcgt cgaataacgt cagcgatctg gccctgaata tcggcggcca tcaggccccg    1920
gacatcctgg tgaagatcgt cggccaggtt gatgtcgcca ctgactttat cgtttaacag    1980
tgcaggtgct aacgcccggc gccggttggc cgggcgttat acaggagacg atatgaaggg    2040
cagcttagcg cacgccgcct tagtggcagg cggcatgatg gttacggggg cagttatggc    2100
cagcagtttg gttcttccca gcgcgcaatc attggcgggg caatggctgg tcgccaatgc    2160
cgaacaacaa tgtcagattg agttttttggc cggtgaacag agtgaaatca acggctactc    2220
attggttgat cggcagcact gtttggaaaa ggtgttaacc gccgaggtgg tcggttggcg    2280
ccctgcaccg gacggcatcg ctttgctgcg ggcggatggc agtacgctgg cgttcttctc    2340
gcgcgatggc gatatttacc gcaaccagct tggcgcggat gacggactga cgctgaaagc    2400
gctggtataa caacagcggg ttcggcagtc gaacccgccc tgagcagcct tacagataca    2460
gcgaacgtac gatcaggaaa t                                              2481
```

PHARMACEUTICAL COMPOSITION CONTAINING ARAZYME FOR THE PREVENTION OF LIVER DYSFUNCTION

CROSS-REFERENCE TO RELATED APPLICATIONS

This application is a divisional application of U.S. patent application Ser. No. 12/521,618, filed Jun. 29, 2009, which is a 371 of PCT/KR2006/005835 filed Dec. 28, 2006, the contents of each of which are all hereby incorporated by reference in their entirety.

TECHNICAL FIELD

The present invention relates to a pharmaceutical composition for the prevention of liver dysfunction which contains arazyme as an active ingredient, more precisely a pharmaceutical composition for the prevention of liver dysfunction which contains arazyme produced by *Aranicola proteolyticus*.

BACKGROUND ART

Chronic liver disease is now a leading cause of death and adult disease in Korea. Liver has a big buffering capacity but once liver disease is developed it does not recognized until it is significantly progressed because there are almost no self-detected symptoms in the early stage of the disease. Make matter worse, no effective therapeutic agent or diagnostic method has been established. Causes of liver disease are alcohol, drugs, chemicals, viral hepatitis, metabolic disease such as biliary track disease and auto-immune disease but there are still more causes unknown. In the meantime, the liver seems to overwork these days as a center of detoxication, blood storage and circulation and the regulation of blood volume, because modern people are more exposed on harmful industrial materials, asking more detoxication, and excessive stresses, alcohol over-drinking, smoking, causing liver damage and further resulting in malfunctioning in immune system and being a cause for another disease.

Complications and hepatoma affecting prognosis in most chronic liver diseases are detected when liver injury is progressed into hepatic fibrosis and hepatic cirrhosis. Therefore, it is important to understand the progress of hepatic fibrosis and to develop a therapeutic agent inhibiting the progress. The therapeutic agents for liver disease in clinical trail are Silymarin produced by Madaus Co., Germany, in 1970s, Ara-AMP produced by Park Davis Co., USA, Carbaica provided by Selvi Co., Italy and DDB provided by Institute of Chinese Materia Medica, China in 1980s, but these drugs carry serious side effects and exhibit low therapeutic effect. Thus, more economical, safe and effective therapeutic agent is in urgent need.

Hepatic fibrosis and liver cirrhosis have been known to be caused by interaction between cytokine and extracellular matrix (ECM). Damaged liver cells induce phagocytosis by kupffer cells, and thus activated kupffer cells secret various cytokines to activate hepatic stellate cells, which has been regarded as a general mechanism in the liver but recent reports add that the damaged liver cells directly activate hepatic stellate cells, so called autocrine. That is, once apoptosis occurs by liver cell damage caused at any reason, TGF-1 is expressed to activate hepatic stellate cells, and then the activated hepatic stellate cells induce TGF-1 expression again that causes apoptosis and this vicious cycle is presumably a cause for serious liver disease (Sun F, et al., *Biochim Biophys Acta*. 2001 Feb. 14; 1535(2):186-191; Jeong W I, et al., *Liver Int*. 2004 December; 24(6):248-254; Marcin Stopa, et al., *J. Biol. Chem*. 2000 September; 29308-29317; Jeong W. I, et al., *Anticancer Res*. 2002 March-April; 22(2A):869-877; Ishak kg, et al., *Alcohol Clin Exp Res*. 1991; 15:45-66; Korean Patent No. 2001-0036463).

To screen a pharmaceutical composition for the prevention of liver dysfunction, studies have been undergoing using microorganisms, plants, and synthetic chemicals, but it still has a long way to go for industrialization, leaving problems including difficulty in obtaining target materials.

The present inventors tried to find a novel protease and as a result the inventors separated a novel microorganism *Aranicola proteolyticus* HY-3 strain (Accession No: KCTC 0268BP; WO 01/57222) from *Nephila clavata*. The present inventors then separated a novel protease Arazyme from the said novel strain. Arazyme not only exhibits excellent protein degradation activity at low temperature and at high salt concentration but also is highly activated at human body temperature of 37° C., in addition to exhibiting very stable activity in wide pH range. The present inventors further identified the gene of this novel protease (WO 01/57222).

The present inventors investigated the effects of arazyme originated from *Aranicola proteolyticus* and completed this invention by confirming that arazyme can protect liver from damages and thereby can be effectively used as a pharmaceutical composition for the prevention of liver dysfunction.

DISCLOSURE

Technical Problem

It is an object of the present invention to provide a novel use of arazyme originated from *Aranicola proteolyticus* as a pharmaceutical composition for the prevention of liver dysfunction.

Technical Solution

To achieve the above object, the present invention provides a pharmaceutical composition for the prevention of liver dysfunction containing arazyme as an active ingredient.

The present invention also provides a method for the treatment of liver disease containing the step of administering the effective dose of the pharmaceutical composition to a liver disease patient.

The present invention further provides health food for the prevention of liver dysfunction containing *Aranicola proteolyticus* culture solution or arazyme isolated therefrom as an active ingredient.

The present invention also provides an apoptosis inhibitor containing arazyme as an active ingredient.

The present invention also provides a P-smad3 expression inhibitor containing arazyme as an active ingredient.

The present invention also provides a liver cell damage inhibitor targeting central vein of the liver which contains arazyme as an active ingredient.

Hereinafter, the present invention is described in detail.

The present invention provides a β-catenin binding RNA aptamer.

The present invention provides a pharmaceutical composition for the prevention of liver dysfunction containing arazyme as an active ingredient.

Arazyme of the invention is an enzyme produced by *Aranicola proteolyticus* and can be prepared by the following steps; 1) preparing the culture solution of *Aranicola proteolyticus* by culturing thereof; 2) obtaining a supernatant by filtering the culture solution; and 3) purifying arazyme in the supernatant using resin (WO 01/57222). The preferable strain to produce arazyme is *Aranicola proteolyticus* and more preferable strain is *Aranicola proteolyticus* HY-3 which has been deposited under the Accession No KCTC 0268BP at Korean Collection for Type Cultures (KCTC) of Korea Research Institute of Bioscience and Biotechnology (KRIBB) by the present inventors on Jul. 29, 1996, but not always limited thereto. *Aranicola proteolyticus* HY-3 is a Gram-negative aerobic bacterium separated from the intestine of a spider, which is 0.5-0.8 mm in size, round shaped, and locomotive. *Aranicola proteolyticus* HY-3 exhibits positive response to catalase but negative response to oxidase (Korean Patent No. 0220091). In the present invention, arazyme obtained by the method described below was used.

Arazyme at the invention is one of (a) the polypeptide harboring the amino acid sequence represented by SEQ ID NO:1; (b) the polypeptide having at least 70% homology with the sequence represented by SEQ ID NO: 1 and equal biological functions as the polypeptide of (a); and (c) the polypeptide which is biologically same as the polypeptide of (a) comprising the amino acid sequence represented by SEQ ID NO: 1 but modified by the substitution, deletion, addition and/or insertion of one or more amino acids therein.

Vitamin C (L-ascorbic acid) has been known to have anti-oxidative effect. When acute liver injury was induced by carbon-tetrachloride ($CCl_4$), the level of vitamin C in the liver was reduced and at the same time oxidative stress caused by carbon-tetrachloride was given to each liver cell, leading to apoptosis or necrosis in liver cells.

SMP30 (Senescence Marker Protein 30) is an in vivo aging marker protein which is expressed largely in liver cells, kidney tubules and epithelial cells. In rats, SMP30 gradually increases in the liver for 12 weeks after birth and its expression is the highest at $12^{th}$ week. Since then, as the rat gets older, SMP30 level gradually decreases. The reduction of SMP30 during the aging is presumably not associated with sex hormones and rather occurs independently. The major functions of the protein are preventing cells from apoptosis, increasing the level of vitamin C by playing a gluconolactonase-like role in vitamin C biosynthesis and increasing in vivo vitamin C synthesis. Vitamin C increased by SMP30 acts as an antioxidant in damaged cells and thereby reduces apoptosis and necrosis. SMP30 is also involved in extracellular elimination of calcium inflowing into cytoplasm during apoptosis, which is eventually helpful to prevent apoptosis.

SMP30 knock-out mice were used to compare the liver protective effects in the absence of SMP30 between vitamin C and arazyme. Vitamin C and arazyme were administered to both wild type C57BL/6(WT) mice and SMP30 knock-out C57BL/6(KO) mice to induce acute liver injury. From the histological observation, inhibition of apoptosis of liver cells was observed, indicating the liver was not seriously damaged (see FIGS. 1 and 2).

In the SMP30 knock-out mouse liver cells, SMP30 immune response was not observed, whereas specific SMP30 immune response was observed in the wild type mouse liver cells. In the meantime, SMP30 was more strongly expressed in mice treated with vitamin C and arazyme than in mice not-treated (see FIGS. 3, 4, 5 and 6). SMP30 has inhibition effect on intracellular calcium accumulation according to cell damage and anti-oxidative activity, so SMP30 expression in arazyme-treated mouse contributes to inhibition of apoptosis and necrosis.

P-smad3 is highly expressed when inflammation and fibrosis are developed by the liver cell damage. Once the liver cells are injured, TGF-1 is synthesized in liver cells, lymphocytes, mast cells and macrophages. Then, TGF-1 binds to TGF-1 receptor II in the liver to activate it. The activated TGF-1 receptor II phosphorylates TGF-1 receptor I, resulting in the activation of TGF-1 receptor I. The phosphorylated TGF-1 receptor I induces consecutive phosphorylation of Smad2 and Smad3, and then phosphorylated Smad2 and Smad3 (P-smad2/3) form a heterooligomer together with Smad4. The heterooligomer migrates into nucleus of the liver cell and stimulates the transcription of a target gene. Thus, strong expression of P-smad3 indicates severe damage in liver cells.

In wild type mouse groups, P-smad3 mediated immune response was strongly observed in $CCl_4$ treated group (G2), compared with the groups treated with vitamin C and arazyme (G3, G4). In SMP30 knock-out mouse groups, P-smad3 mediated immune response was strongly detected in the groups treated with $CCl_4$ alone or together with vitamin C (G6, G7), compared with the group (G8) treated with arazyme (see FIGS. 7, 8, 9 and 10). This result indicates that SMP30 knock out mice exhibit more severe liver cell damage even under same stimulation of $CCl_4$. P-smad3 level was lower in the mouse group treated with arazyme than in the group treated with vitamin C. This result supports the founding that arazyme inhibits chronic inflammation by TGF-1 and has excellent liver cell protective effect. In the meantime, Smad levels in liver cells did not differ between wild type mouse groups and SMP30 knock out mouse groups (see FIGS. 11, 12 and 13).

CYP2E1 expression was increased only in the arazyme treated mouse liver cells (see FIGS. 14 and 15). That is, in the arazyme-non-treated group, apoptosis and necrosis were already undertaken in liver cells around central vein region, so that CYP2E1 was not expressed anymore. On the other hand, in the arazyme treated group, only weak injury was observed in liver cells around central vein region owing to the protective effect of arazyme, resulting in moderate CYP2E1 expression.

Metabolism of $CCl_4$ starts with the procedure in which electrons from C—Cl bond form a radical by cytochrome P450 (CYP). Trichloromethyl radical can be either oxidized or reduced. CYP2E1 and 2B1/2B2 inactivate $CCl_4$, by which CYP2E1 level is reduced and therefore CYP2E1 expression is continuously induced.

As explained hereinbefore, arazyme treatment inhibits necrosis of the injured liver cell, increases SMP30 expression, reduces P-smad3 expression and induces CYP2E1 expression by preventing liver cell injury caused by chemicals particularly in the area of central vein. Therefore, it is understood that arazyme of the present invention has liver protective effect. Arazyme was also orally administered to female Wistar rats to investigate toxicity. AS a result no abnormal symptoms were observed by the naked eye pathological observations at the concentrations of 0, 1,250, 2,500 and 5,000 mg/kg. Therefore, the arazyme used in this experiment was evaluated to be safe substance and its estimated $LD_{50}$ value is much greater than 5,000 mg/kg in rats. Thus, arazyme of the present invention can be used as a pharmaceutical composition for the prevention of liver dysfunction and further for the prevention and treatment of liver diseases such as acute hepatitis, chronic hepatitis, fatty liver, liver cirrhosis, hepatic coma, alcoholic liver disease and hepatoma.

The composition of the present invention can additionally include, in addition to arazyme, one or more active ingredients having the same or similar functions to the arazyme of the invention. For the administration, the composition of the present invention can also include one or more pharmaceutically acceptable carriers. The pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc, can be added. In order to prepare injectable solutions such as aqueous solution, suspension and emulsion, pills, capsules, granules or tablets, diluents, dispersing agents, surfactants, binders and lubricants can be additionally added. The composition of the present invention can further be prepared in suitable forms for each disease or according to ingredients by following a method represented in Remington's Pharmaceutical Science (Mack Publishing Company, Easton Pa., 18th, 1990).

The present invention also provides a method for the treatment of liver disease containing the step of administering the effective dose of the pharmaceutical composition to a liver disease patient. Herein the liver disease includes acute hepatitis, chronic hepatitis, fatty liver, liver cirrhosis, hepatic coma, alcoholic liver disease and hepatoma.

The pharmaceutical composition for the prevention of liver dysfunction of the present invention can be administered orally or parenterally (for example, intravenous, hypodermic, local or peritoneal injection). The effective dosage of the composition can be determined according to weight, age, gender, health condition, diet, administration frequency, administration method, excretion and severity of a disease. The dosage of arazyme of the invention is 0.01-5000 mg/kg per day, and preferably 0.01-10 mg/kg per day. Administration frequency is once a day or preferably a few times a day, but not always limited thereto and can be changed by the doctor in charge.

The present invention further provides a health food for the prevention of liver dysfunction containing *Aranicola proteolyticus* culture solution or arazyme isolated therefrom as an active ingredient.

The *Aranicola proteolyticus* culture solution or arazyme isolated therefrom can be used as a food additive. At this time, the *Aranicola proteolyticus* culture solution or arazyme isolated therefrom can be added as it is or after being mixed with other food or ingredients, according to the conventional method. The mixing ratio of active ingredients is determined by the purpose of use (prevention, health or therapeutic treatment). In the case of producing food or beverages, the *Aranicola proteolyticus* culture solution or arazyme isolated therefrom is preferably added by 0.01-10 weight part, more preferably by 0.05-1 weight part, to the raw material. However, the content might be less than the above when it is administered for long-term to improve health conditions but the effective dosage could contain more than the above amount because the culture solution or the enzyme of the invention is very safe.

There is no limit in applicable food, which is exemplified by meats, sausages, bread, chocolate, candies, snacks, cookies, pizza, ramyun, noodles, dairy products including ice cream, soups, beverages, tea, drinks, alcoholic drinks and vitamin complex, etc, and in fact every health food generally produced are all included.

Health beverages containing the *Aranicola proteolyticus* culture solution or arazyme isolated therefrom of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. As a sweetener, either natural sweetener such as thaumatin and stevia extract or artificial sweetener such as saccharin and aspartame can be used. The ratio of natural carbohydrate to the composition of the present invention is preferably 0.01-0.04 g to 100 ml, more preferably 0.02-0.03 g to 100 ml.

In addition to the ingredients mentioned above, the *Aranicola proteolyticus* culture solution or arazyme isolated therefrom of the present invention can include in variety of nutrients, vitamins, electrolytes, flavoring agents, coloring agents, pectic acid and its salts, arginic acid and its salts, organic acid, protective colloidal viscosifiers, pH regulators, stabilizers, antiseptics, glycerin, alcohols, carbonators which used to be added to soda, etc. The *Aranicola proteolyticus* culture solution or arazyme isolated therefrom of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.01-0.1 weight part per 100 weight part of the *Aranicola proteolyticus* culture solution or arazyme isolated therefrom of the invention.

The present invention also provides an apoptosis inhibitor containing arazyme as an active ingredient.

The present invention also provides a P-smad3 expression inhibitor containing arazyme as an active ingredient.

The present invention also provides a liver cell damage inhibitor targeting central vein of the liver which contains arazyme as an active ingredient.

DESCRIPTION OF DRAWINGS

The application of the preferred embodiments of the present invention is best understood with reference to the accompanying drawings, wherein.

G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

Figure 10:
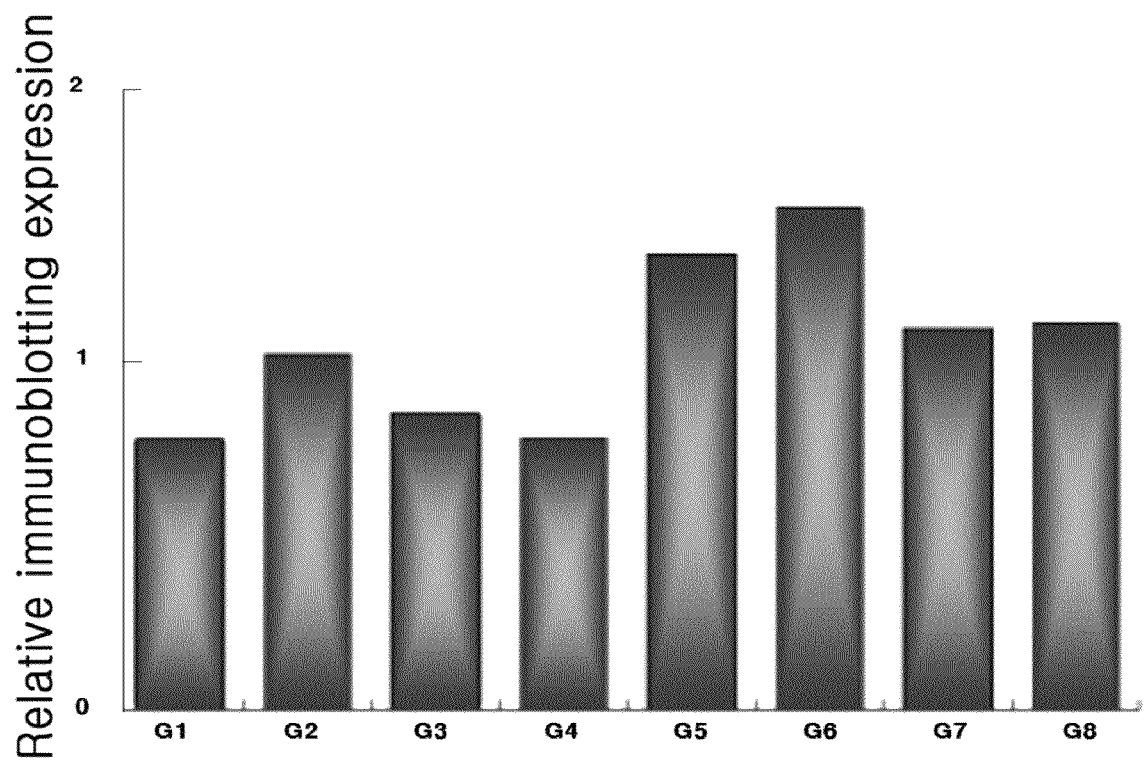

FIG. 10 is a graph illustrating the expression of P-smad3 detected by immunoblotting, G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

Figure 11:
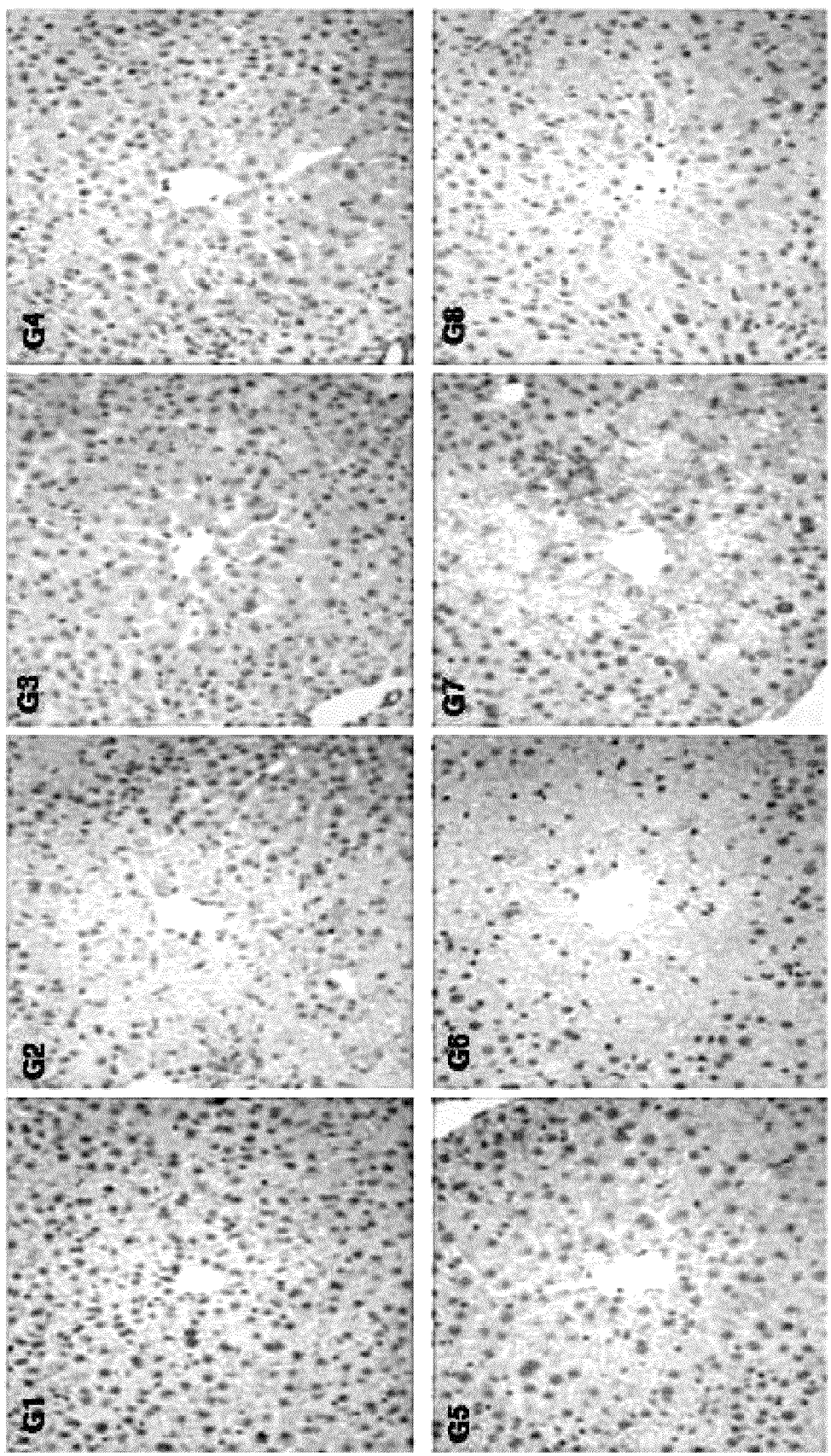

FIG. 11 is a set of immunohistological photographs illustrating Smad3 expression in the wild type and SMP30 knock out mice with acute liver injury (magnification: ×66), G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

Figure 12:
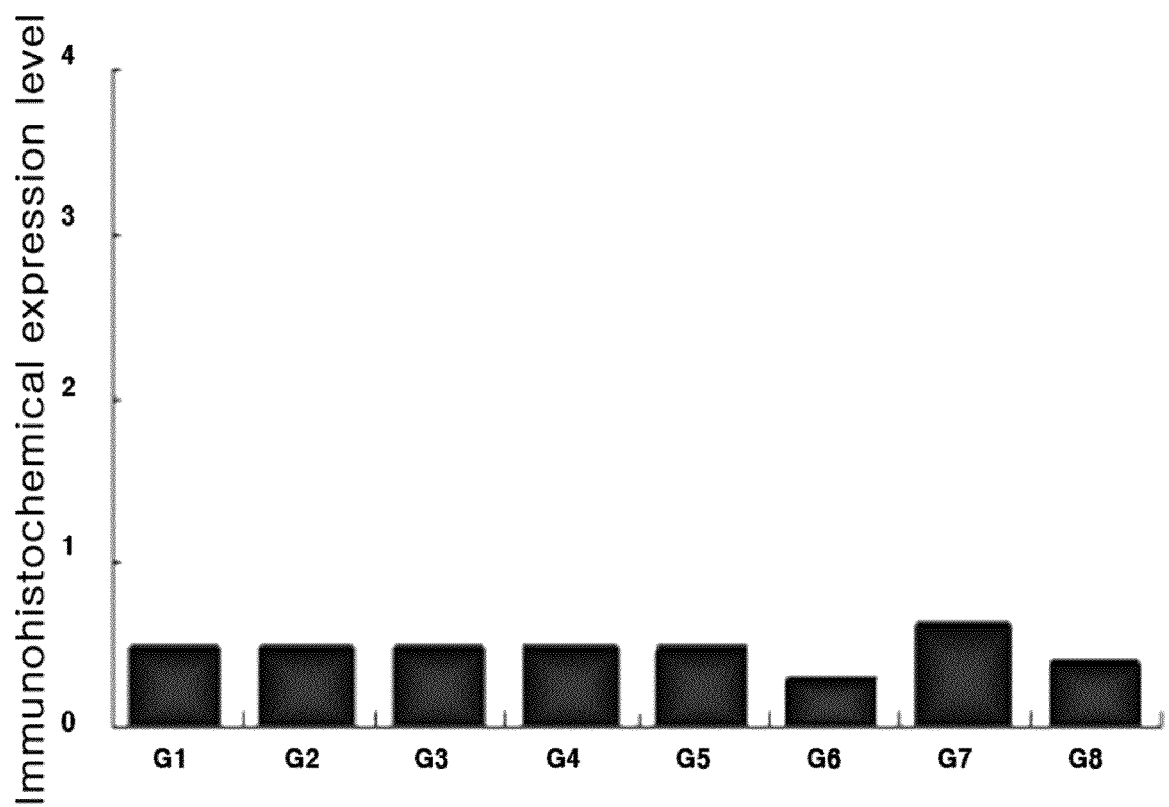

FIG. 12 is a graph illustrating the expression of Smad3 detected by immunohistological approach, G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

Figure 13:
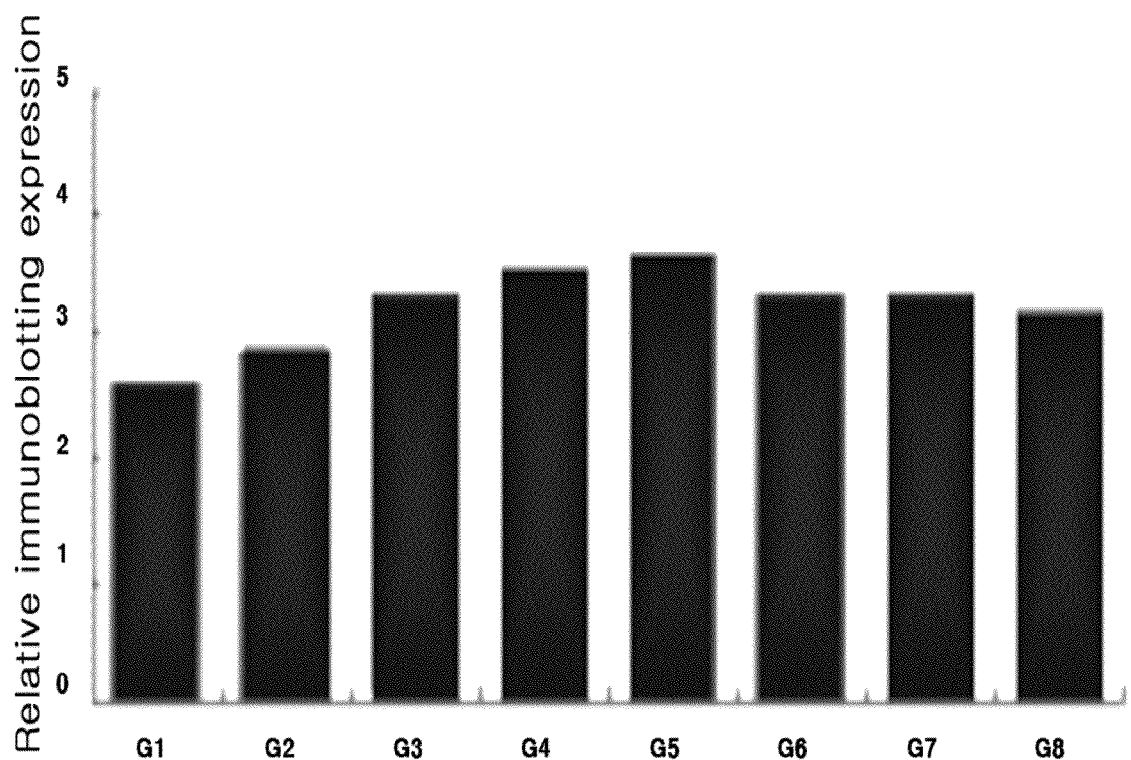

FIG. 13 is a graph illustrating the expression of Smad3 detected by immunoblotting, G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

Figure 14:
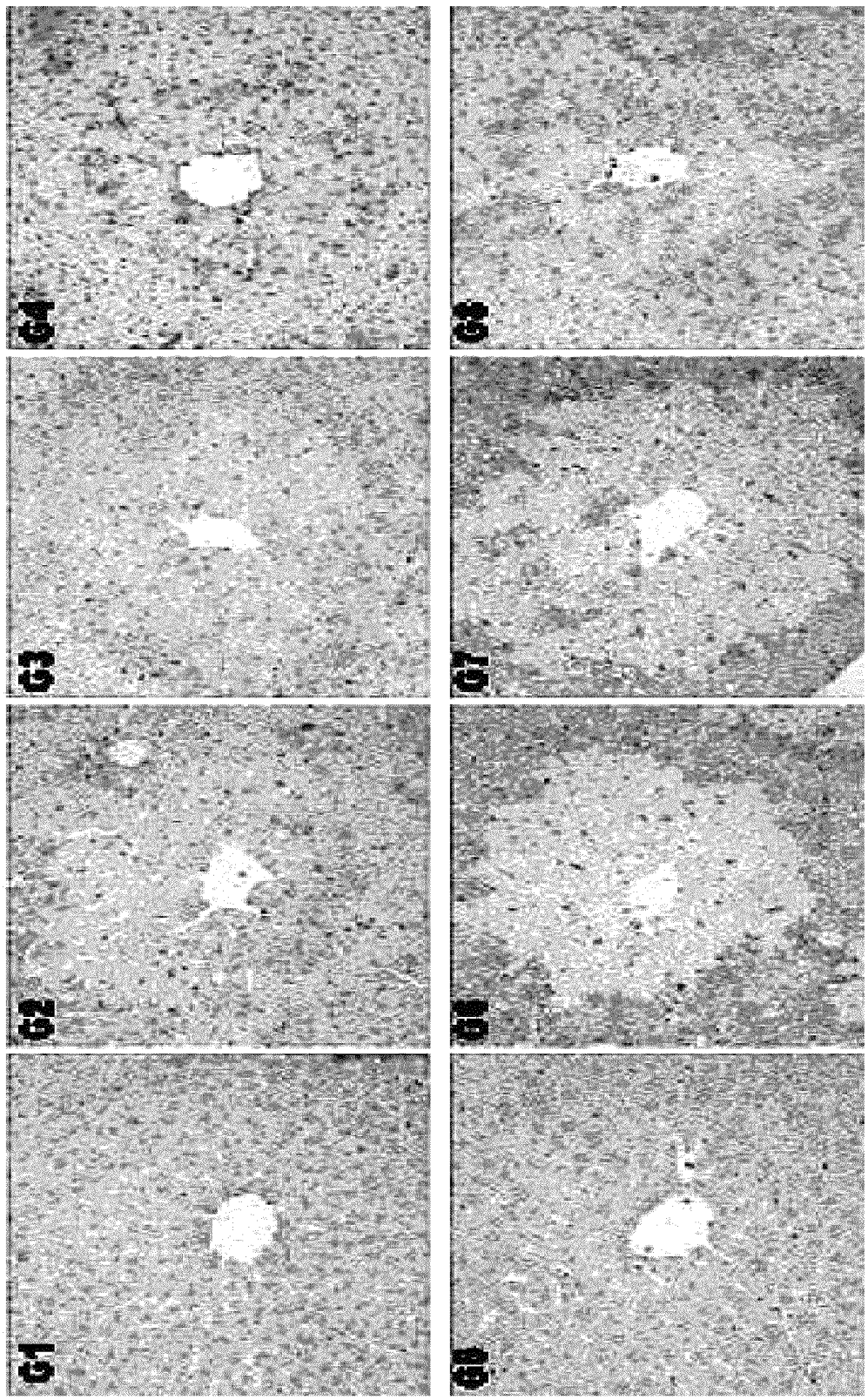

FIG. 14 is a set of immunohistological photographs illustrating CYP2E1 expression in the wild type and SMP30 knock out mice with acute liver injury (magnification: ×66), G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

Figure 15:
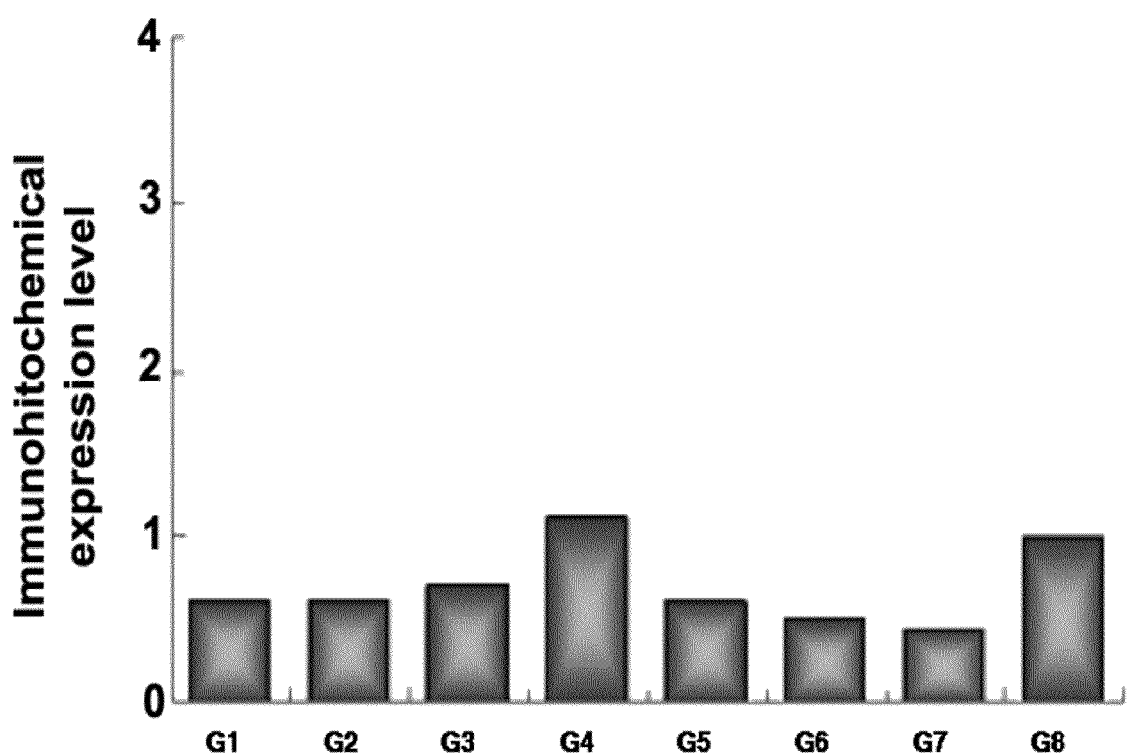

FIG. 15 is a graph illustrating the expression of CYP2E1 detected by immunohistological approach.

G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Production of Arazyme

To produce the active ingredient 'arazyme', Aranicola proteolyticus HY-3 (KCTC 0268BP) was cultured in a culture medium (bacto trypton 0.5%, yeast extract 0.5%, sodium chloride 0.1%, potassium chloride 0.5%, calcium chloride 0.02%, magnesium sulfate 0.02%) at 22° C. for 18 hours. The supernatant and cells were separated from the culture solution by membrane filtration using a 2 μm membrane filter. The separated supernatant was concentrated by 10 kDA membrane filtration. Arazyme of the present invention basically exhibits the characteristics of anions. So, arazyme was purified by ion exchange resin using DEAE-cellulose pre-treated with 50 mM tris-HCl buffer (pH 7.6) and gel filtration exchange resin using Sephadex G-75 pre-treated with 20 mM tris-HCl buffer (pH 7.6). The purified enzyme solution proceeded to 10% SDS-PAGE (Sodium dodecyl sulfate-polyacrylamide gel) for electrophoresis. As a result, it was confirmed that arazyme of the present invention was a monomer without a subunit and showed a band of 51.5 kDa. To produce arazyme, Aranicola proteolyticus HY-3 strain (KCTC 0268BP) can be cultured in various industrial media and its culture solution can be separated and purified by different methods generally known. Arazyme at the present invention has a polypeptide sequence represented by SEQ ID NO: 1 and a polynucleotide sequence represented by SEQ ID NO: 2.

Experimental Example 1

Constitution of Experimental Groups and Administration

SMP30 is an important marker protein for aging and is involved in vitamin C biosynthesis, suggesting that SMP30 acts as an antioxidant by increasing vitamin C synthesis. In the present invention, male wild type C57BL/6(WT) at 12 weeks and SMP30 knock-out C57BL/6(KO) mice were used to induce liver injury by $CCl_4$ and then the relation of SMP30 with arazyme was investigated. 10 male and 20 female SMP30 knock-out C57BL/6 mice were distributed from Tokyo Metropolitan Institute of Gerontology, which were then raised in the animal laboratory at Department of Pathology, College of Veterinary Medicine, Kyungpook National University, Korea. Among F1 mice generated by breeding, knock-out mice were selected by tail DNA genotyping by PCR.

Wild type mice were quarantined and adapted for 7 days in the animal laboratory. During the adaptation, every symptom was checked and only healthy animals were selected. Both wild type and SMP30 knock-out mice were 12 weeks old, excluding the difference in age.

Rats were adapted and raised in an animal facility where temperature was regulated to 22±3° C., humidity was adjusted to 55±10% and light was also regulated to 12L/12D (08:00 lights on, 20:00 lights out). The environmental conditions were checked regularly (every three months). After environmental evaluation, no changes in important conditions were recognized. During the whole experiment period, rats were raised in polycarbonate cages [240 W×390 L×175 H (mm)] by up to 5 per cage. Skin mark using an oil magic pen and individual identification card were used for distinguishment. Feed for laboratory animals (PMI Nutrition International, 505 North 4th Street Richmond, in 47374, USA) was provided at any time after being sterilized by irradiation (13.2 kGy). Tap water was provided using a water bottle at any time after being purified by a carbon filter. Carbon tetrachloride was diluted in olive oil at the concentration of 0.4 ml/kg and administered to rats once to induce liver injury. 24 hours after the administration, autopsy was performed.

Wild type mice and SMP30 knock-out mice were divided, by 5 of each, into negative control groups (G1, G5), positive control groups (G2, G6), two of experimental group 1 (G3, G7) and two of experimental group 2 (G4, G8) (Table 1). Intraperitoneal administration of olive oil was performed once to negative control mice (G1, G5), while intraperitoneal administration of $CCl_4$ (0.4 ml/kg) was performed once to positive control mice (G2, G6). In the meantime, 100 mg/kg of vitamin C dissolved in tap water was orally administered to experimental group 1 mice (G3, G7) one day before the intraperitoneal administration of $CCl_4$ (0.4 ml/kg). 100 mg/kg of arazyme dissolved in tap water was orally administered to experimental group 2 mice (G4, G8) one day before the intraperitoneal administration of $CCl_4$ (0.4 ml/kg). 24 hours after the administration of $CCl_4$, autopsy was performed in every mouse and samples were taken from each mouse for histopathological test.

Constitution of experimental groups was as shown in Table 1.

TABLE 1

Constitution of experimental groups

| Group | Condition | Number of mice | Treatment |
|---|---|---|---|
| G1 | Wild type + Tap water | 5 | Olive oil |
| G2 | Wild type + Tap water | 5 | $CCl_4$ |
| G3 | Wild type + Tap water | 5 | Vitamin C, $CCl_4$ |
| G4 | Wild type + Tap water | 5 | Arazyme, $CCl_4$ |
| G5 | SMP30 knock-out + Tap water | 5 | Olive oil |
| G6 | SMP30 knock-out + Tap water | 5 | $CCl_4$ |
| G7 | SMP30 knock-out + Tap water | 5 | Vitamin C, $CCl_4$ |
| G8 | SMP30 knock-out + Tap water | 5 | Arazyme, $CCl_4$ |

Animals: 12 weeks old, male, wild type C57BL/6 mice and SMP30 knock-out (KO) C57BL/6 mice Treatment of arazyme: oral administration (100 mg/kg) before the administration of $CCl_4$ Treatment of vitamin C: oral administration (100 mg/kg) before the administration of $CCl_4$ Treatment of $CCl_4$: intraperitoneal administration (0.4 ml/kg=10% $CCl_4$ 4 ml/kg)

Experimental Example 2

Histopathological Observation on Liver Cells

To examine the effect of arazyme on liver injury by $CCl_4$ according to histopathological test, each liver sample taken from autopsy was fixed in 10% neutral formalin and the fixed tissues were treated by the automatic tissue processor. The treated liver cells were paraffin-embedded and cut into 4 μm thick sections. The sections were dried and stained with hematoxylin-eosins (H&E staining), followed by observation under optical microscope.

Figure 1:
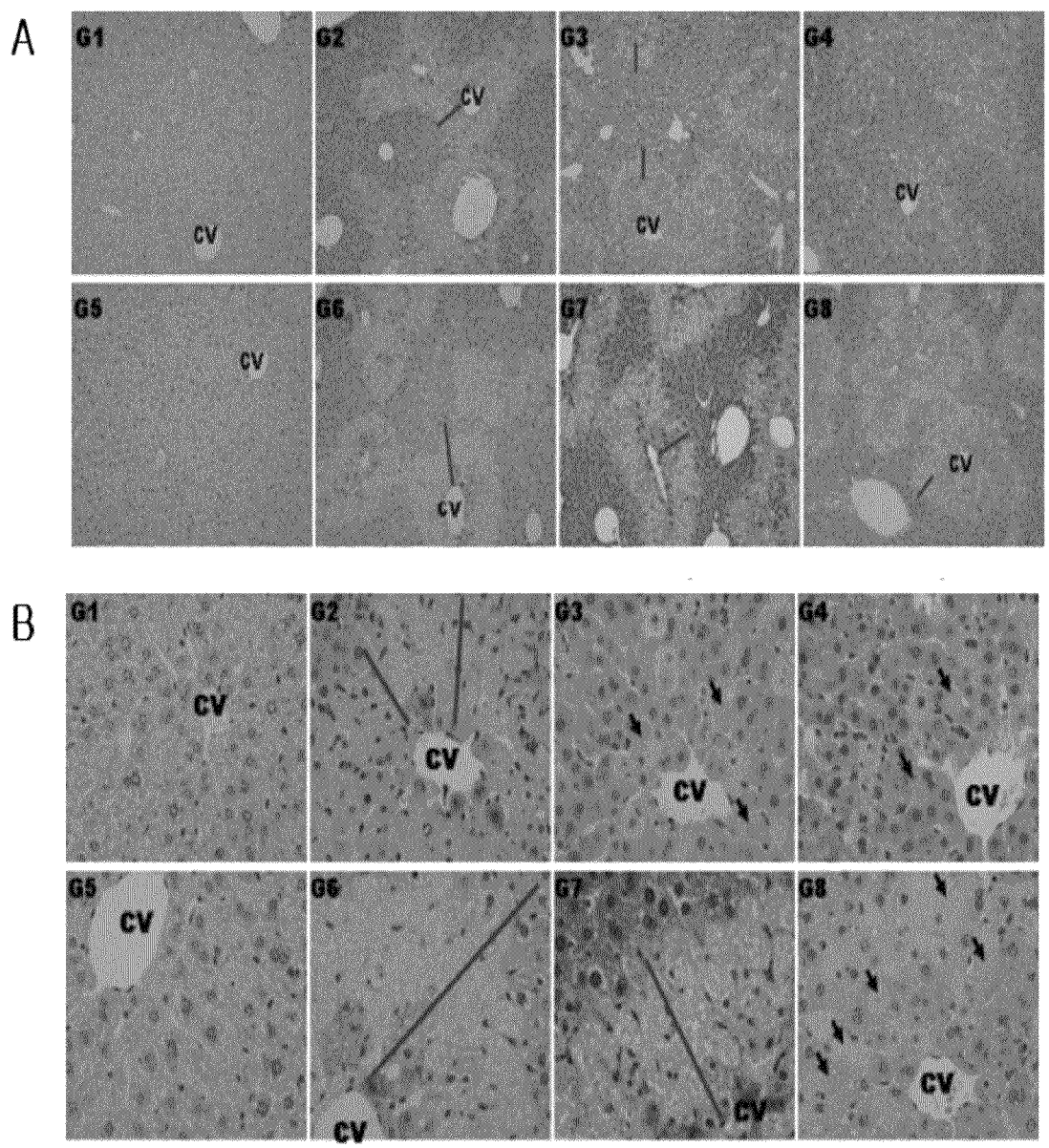
FIG. 1 is a set of histological photographs illustrating the livers of the wild type mice (WT) and the SMP30 knock out (KO) mice with acute liver injury (H&E staining, A: magnification×33, B: magnification×132), G1: wild type mice, olive treated; G2: wild type mice, $CCl_4$ treated; G3: wild type mice, vitamin C and $CCl_4$ treated; G4: wild type mice, arazyme and $CCl_4$ treated; G5: SMP30 knock-out mice, olive treated; G6: SMP30 knock-out mice, $CCl_4$ treated; G7: SMP30 knock-out mice, vitamin C and $CCl_4$ treated; G8: SMP30 knock-out mice, arazyme and $CCl_4$ treated; Red line: necrotizing area around central vein (CV) region; and Arrow: injured liver cells.
Figure 2:
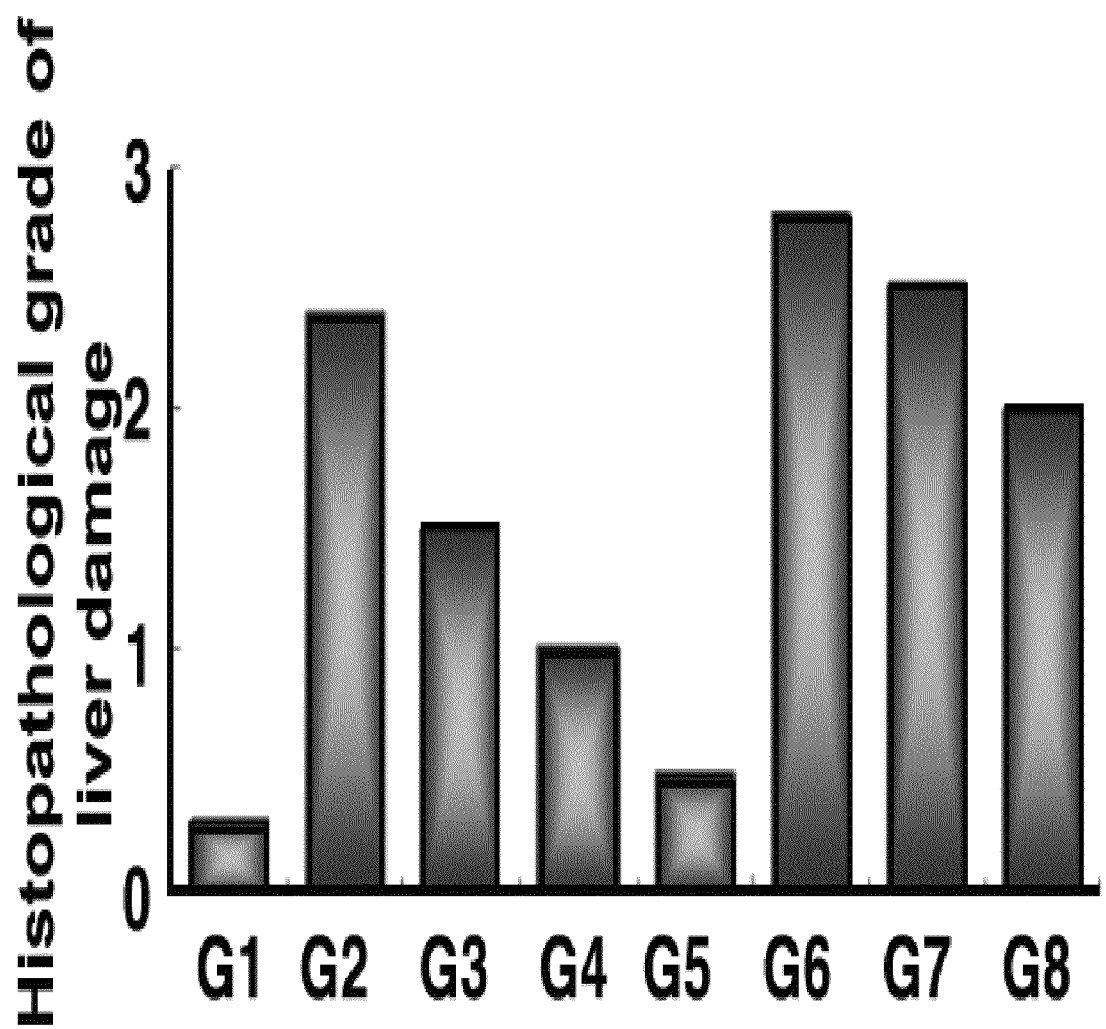
FIG. 2 is a graph illustrating numerical values presenting liver injury observed by histopathological approach, G1: wild type mice, olive treated; G2: wild type mice, $CCl_4$ treated; G3: wild type mice, vitamin C and $CCl_4$ treated; G4: wild type mice, arazyme and $CCl_4$ treated; G5: SMP30 knock-out mice, olive treated; G6: SMP30 knock-out mice, $CCl_4$ treated; G7: SMP30 knock-out mice, vitamin C and $CCl_4$ treated; G8: SMP30 knock-out mice, arazyme and $CCl_4$ treated; extent of liver injury 0: no proof of injury according to morphological observation; extent of liver injury 1: sporadic necrosis in 5 liver cells around central vein region; extent of liver injury 2: even necrosis in 5 liver cells around central vein region and in non-injured area; and extent of liver injury 3: wide necrosis in the liver including 5 liver cells around central vein region and the central part.

As a result, centrilobular necrosis and inflammation were observed in SMP30 knock-out mice (G5, G8), compared with wild type mice (G1, G4). And necrosis in liver cells was significantly inhibited in both wild type mice (G1, G4) and SMP30 knock-out mice (G5, G8) treated with vitamin C and arazyme (FIGS. 1 and 2).

Numerical values on liver injury obtained from histopathological observation are shown in Table 2.

TABLE 2

Numerical values on liver injury obtained by histopathological observation

| Level | Extent of liver injury |
|---|---|
| 0 | No morphological proof of liver injury was detected. |
| 1 | Even but sporadic necrosis was observed in 5 liver cells around central vein region. |
| 2 | Even necrosis was detected in 5 liver cells around central vein region and non-injured area. |
| 3 | Wide necrosis was observed in overall liver cells including the central part in addition to 5 liver cells around central vein region. |

Experimental Example 3

Expression of SMP30 in Liver Cells

<3-1> Immunohistochemical Observation with SMP30 in Liver Cells

To observe SMP30 in liver cells immunohistochemically, paraffin embedded tissues fixed with formalin were cut into 4 μm thick sections, followed by deparaffinization. To inhibit the activity of endogenous peroxidase, the sections were treated in 3% $H_2O_2$ for 30 minutes and washed with 0.01 M PBS. To increase antigen expression of the tissues, the sections were treated with 0.01 M citrate buffer, followed by heat treatment using microwave. To inhibit non-specific reaction, the sections were treated with 20 g/ml of proteinase K at 37° C. for 10 minutes and washed with PBS, followed by blocking for one hour. Then, the primary antibody SMP30 (1:5000, Akihito Ishigami, Japan) was treated thereto at 4° C. for overnight, then washed three times with PBS for 5 minutes. And the primary antibody was bound to biotin. The biotin labeled primary antibody was washed with buffer, adhered to streptavidin conjugated HRP (Horse-Radish Peroxidase), washed with buffer again, followed by reaction at 30° C. for 30 minutes using Histostantin-plus bulk kit (Zymed Laboratories Inc, USA). After completely washing, the samples were colored with 3,3-diaminobenzidine tetrahydrochloried (DAB, Zymed Laboratories Inc, USA) solution, washed with distilled water, and counter-stained with Meyer's hematoxylin (Research genetics, USA), followed by observation under optical microscope.

Figure 3:
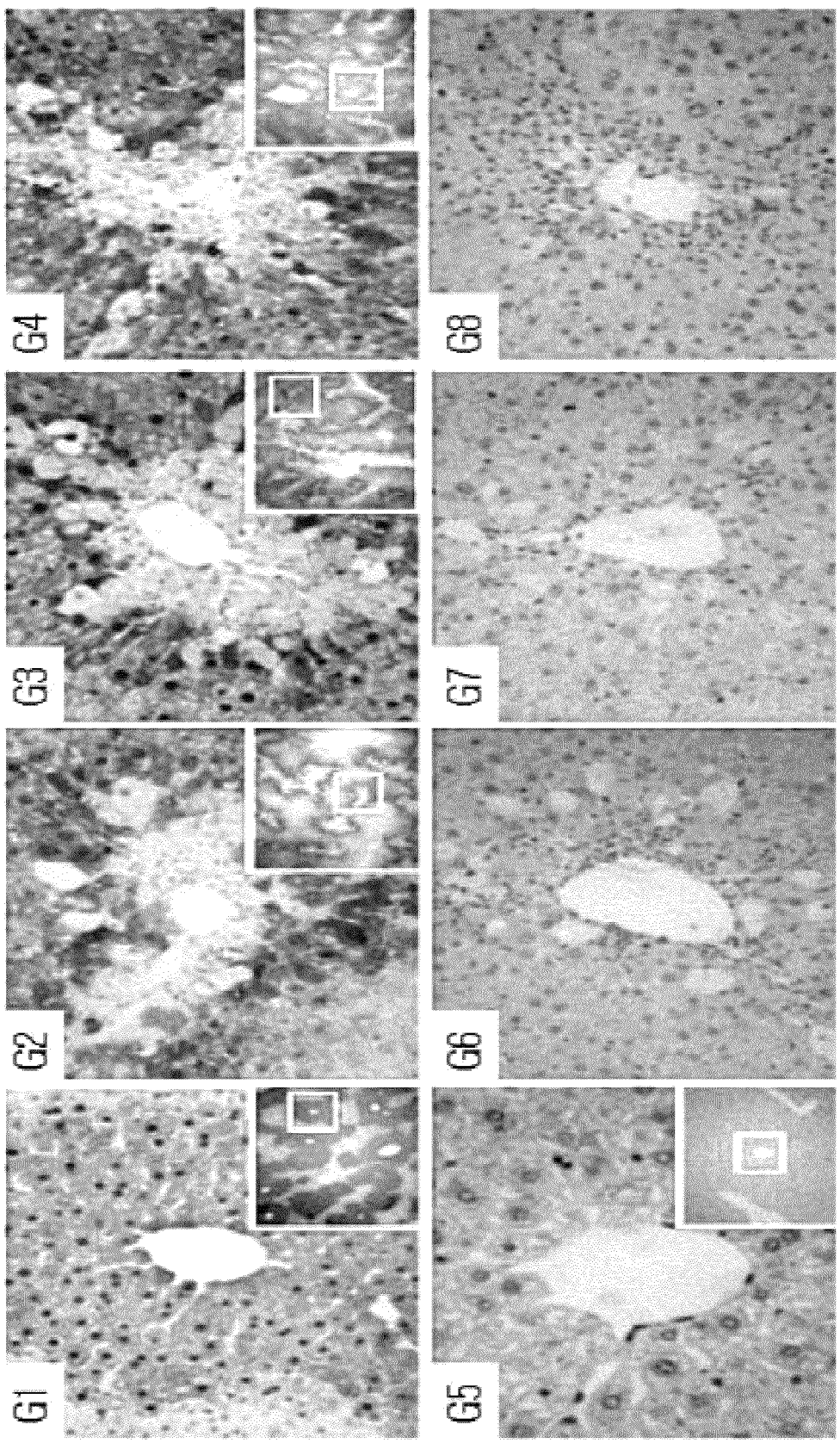
FIG. 3 is a set of immunohistological photographs illustrating SMP30 expression in the wild type and SMP30 knock out mice with acute liver injury (magnifications: ×13.2 and ×66), G1: wild type mice, olive treated; G2: wild type mice, $CCl_4$ treated; G3: wild type mice, vitamin C and $CCl_4$ treated; G4: wild type mice, arazyme and $CCl_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.
Figure 4:
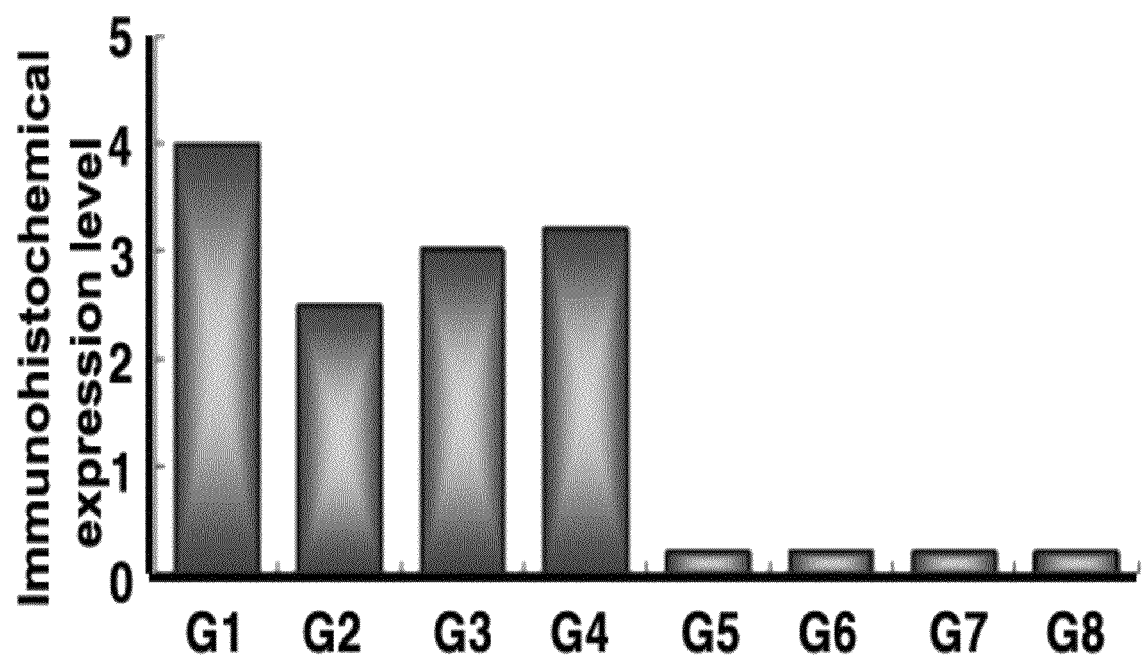
FIG. 4 is a graph illustrating the expression of SMP30 detected by immunohistological approach, G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

From the immunohistochemical observation on SMP30, it was confirmed that SMP30 mediated immune response was not observed in SMP30 knock-out mice, while immune response positive to SMP30 was observed specifically in liver cells in wild type mice (FIGS. 3 and 4). The level of SMP30 expression in the wild type negative control (G1) was much higher that than in the group with liver injury by $CCl_4$ (G2). In the meantime, the levels of SMP30 expression in groups treated with vitamin C or arazyme (G3, G4) were higher than those in positive controls (G2, G6) treated with $CCl_4$ alone.

<3-2> Expression of SMP30 in Liver Cells Investigated by Immunoblotting

The expression of SMP30 in liver cells was investigated by immunoblotting. First, the liver tissues frozen at −70° C. were homogenized in RIPA buffer containing 0.1 mM sodium orthovandate ($Na_3VO_4$) and protease inhibitor cocktail tablet (Roche, Mannheim, Germany). The homogenated liver samples were centrifuged at 4° C. with 4,000 rpm for 10 minutes to eliminate fat and supernatant was obtained. The supernatant was centrifuged again at 4° C. with 14,000 rpm for 20 minutes, supernatant was separated again. Protein concentration was measured by Bradford method and each protein sample proceeded onto 10% SDS-polyacrylamide gel at the concentration of 80 g/well, followed by electrophoresis. The protein in the gel was electro-transferred onto PVDF membrane (Schleicher & Chuell, Dassel, Germany). Equal amount of protein was loaded, confirmed by Coomassie blue staining. Blocking was performed with a blocking solution (PBS containing 3% bovine serum albumin) for 1 hour, followed by reaction with SMP30 (1:5,000, Akihito Ishigami, Japan) and β-Actin (1:500 Santa Cruz Biotechnology Inc, USA). After washing with TBS buffer containing 0.5% Tween 200, the membrane was reacted with anti-rabbit-HRP-antibody (1:1,000-1:2,000, Akihito Ishigami, Japan), the secondary antibody, at room temperature for one hour. The membrane was completely washed with TBS buffer and reacted with super signal West Dura Extended Duration Substrate (PIERCE, USA) and exposed on clinical X-ray film (Kodak, Tokyo, Japan) to investigate any specific reactions.

Figure 5:
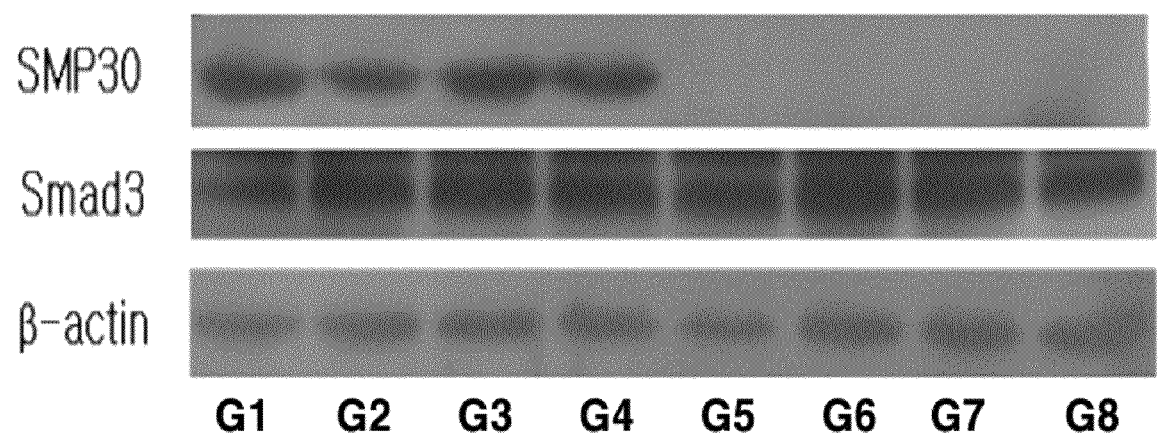
FIG. 5 is a set of photographs illustrating the result of immunoblotting with SMP30 in the wild type and SMP30 knock out mice with acute liver injury, G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.
Figure 6:
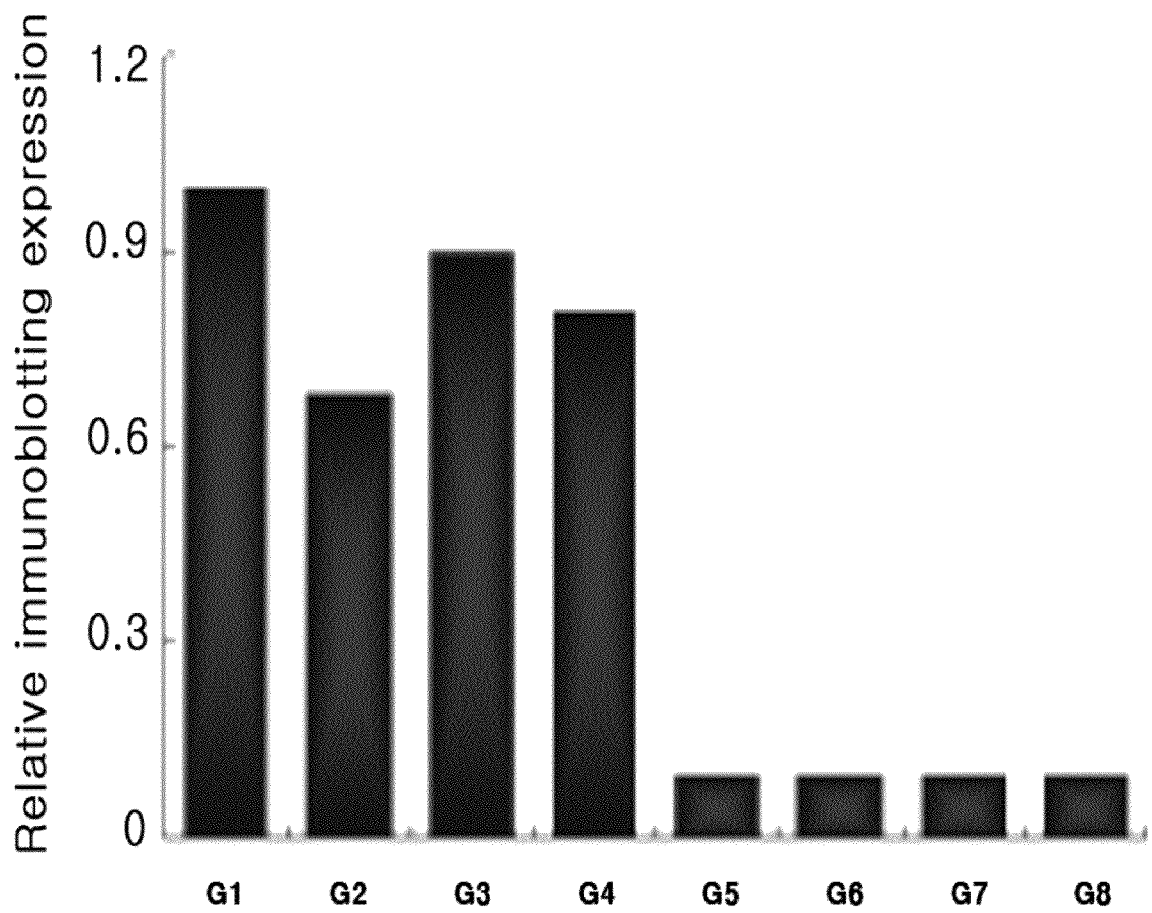
FIG. 6 is a graph illustrating the expression of SMP30 detected by immunoblotting, G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

As a result, SMP30 expression was detected in wild type mice but not in SMP30 knock-out mice (FIGS. 5 and 6).

SMP30 expression was highest in the negative control treated with olive oil only among wild type mouse groups, but SMP30 expression was inhibited in group 2 (G2) treated with $CCl_4$ alone. In the meantime, SMP30 expression was also high in groups treated with vitamin C (G3) and arazyme (G4), compared with the group treated with $CCl_4$ only.

Experimental Example 4

Expression of P-Smad3 in Liver Cells

<4-1> Immunohistochemical Observation of P-Smad3 Expression in Liver Cells

To investigate P-smad3 expression in liver cells by immunohistochemical approach, experiments were performed by the same manner as described in Experimental Example <3-1> except that P-smad3 (1:200, Cell Signaling Technology Inc, USA) was used as primary antibody instead of SMP30.

Figure 7:
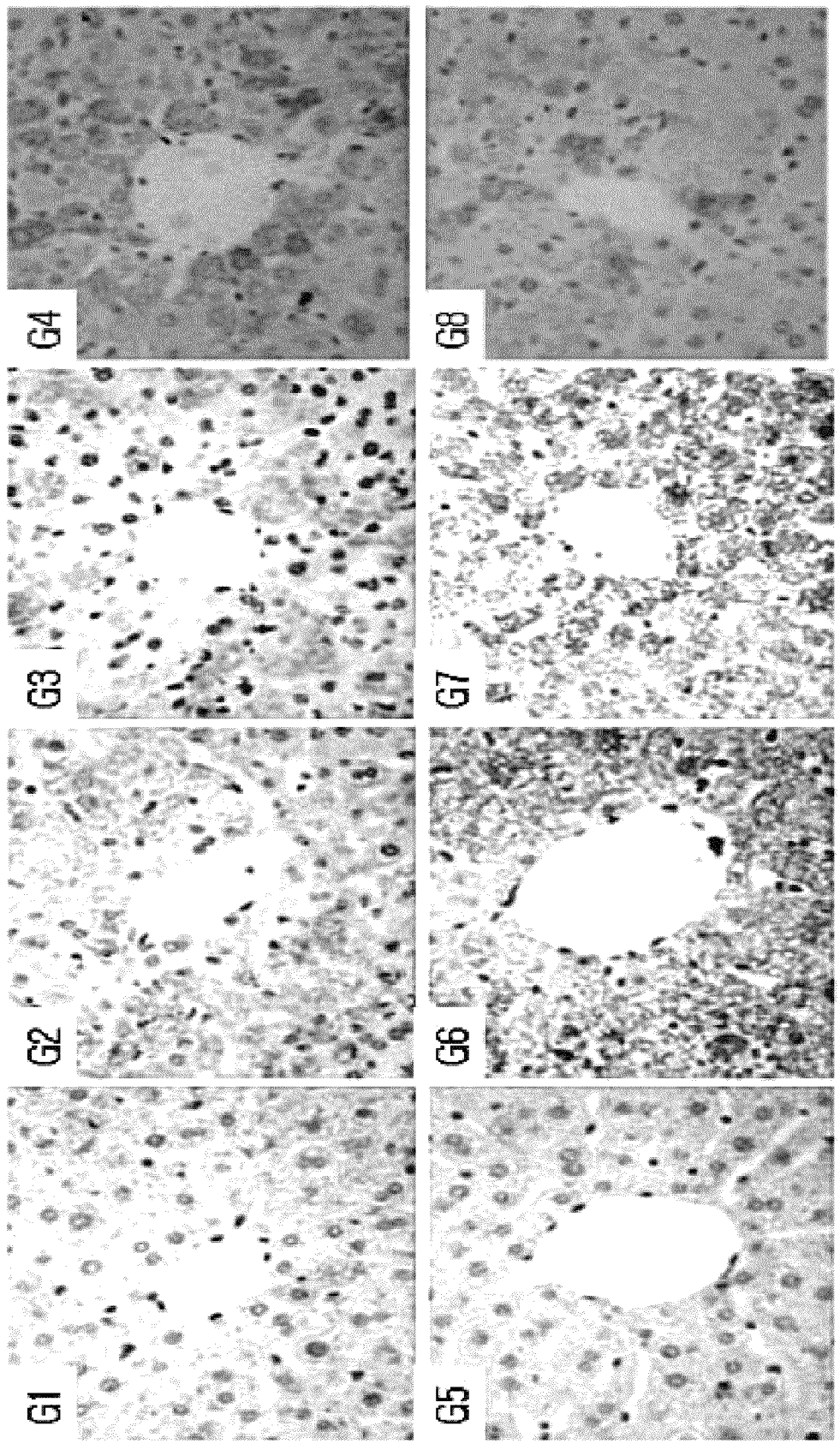
FIG. 7 is a set of immunohistological photographs illustrating P-smad3 in the wild type and SMP30 knock out mice with acute liver injury, G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.
Figure 8:
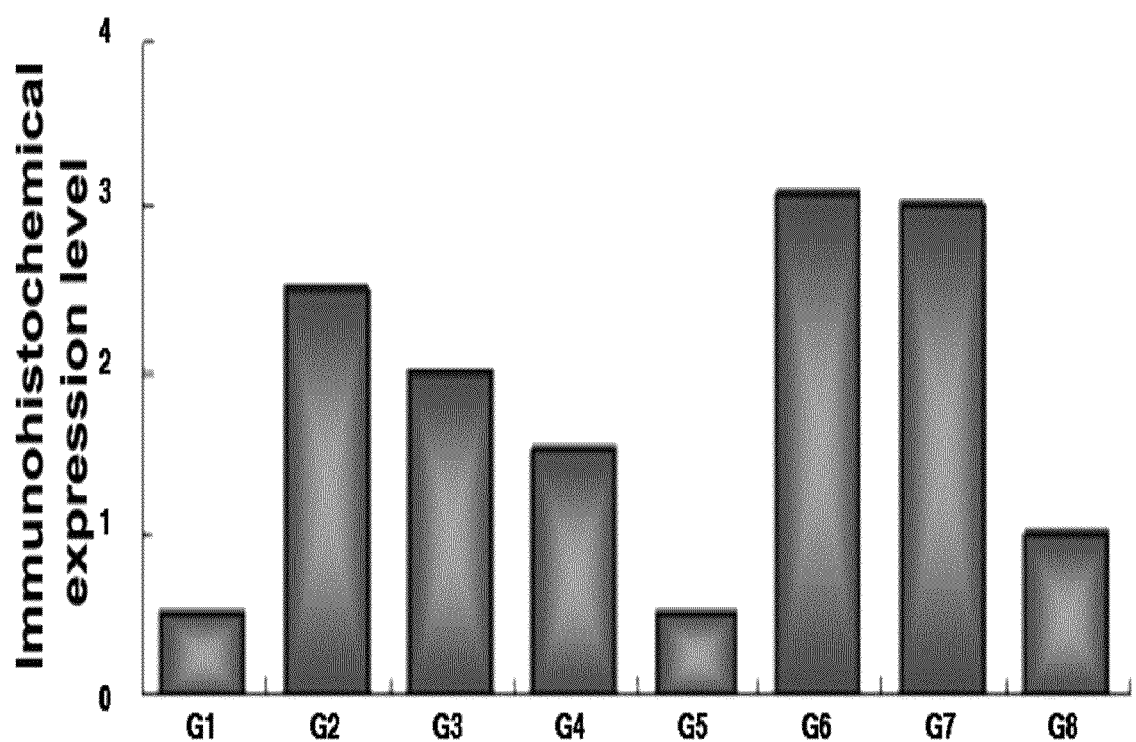
FIG. 8 is a graph illustrating the expression of P-smad3 detected by immunohistological approach, G1: wild type mice, olive treated; G2: wild type mice, CCl$_4$ treated; G3: wild type mice, vitamin C and CCl$_4$ treated; G4: wild type mice, arazyme and CCl$_4$ treated; G5: SMP30 knock-out mice, olive treated; G6: SMP30 knock-out mice, CCl$_4$ treated; G7: SMP30 knock-out mice, vitamin C and CCl$_4$ treated; G8: SMP30 knock-out mice, arazyme and CCl$_4$ treated.

As a result, strong immune response against P-smad3 was detected in group 2 (G2) treated with $CCl_4$ only, compared with the groups (G3, G4) treated with vitamin C and arazyme among wild type mouse groups. Among SMP30 knock-out mice, the immune response was strongly detected in groups (G6, G7) treated with $CCl_4$ alone or vitamin C, compared with the group (G8) treated with arazyme (FIGS. 7 and 8). The P-smad3 expression was lower in the groups treated with arazyme (G4, G8) than in the groups treated with vitamin C (G3, G7).

<4-2> Expression of P-Smad3 in Liver Cells Detected by Immunoblotting

To investigate P-smad3 expression in liver cells by immunoblotting, experiments were performed by the same manner as described in Experimental Example <3-2> except that P-smad3 (1:200, Cell Signaling Technology Inc, USA) was used as primary antibody instead of SMP30 and anti-rabbit-HRP-antibody (1:1,000-1:2,000, Cell Signaling Technology Inc, USA) was used as secondary antibody.

Figure 9:
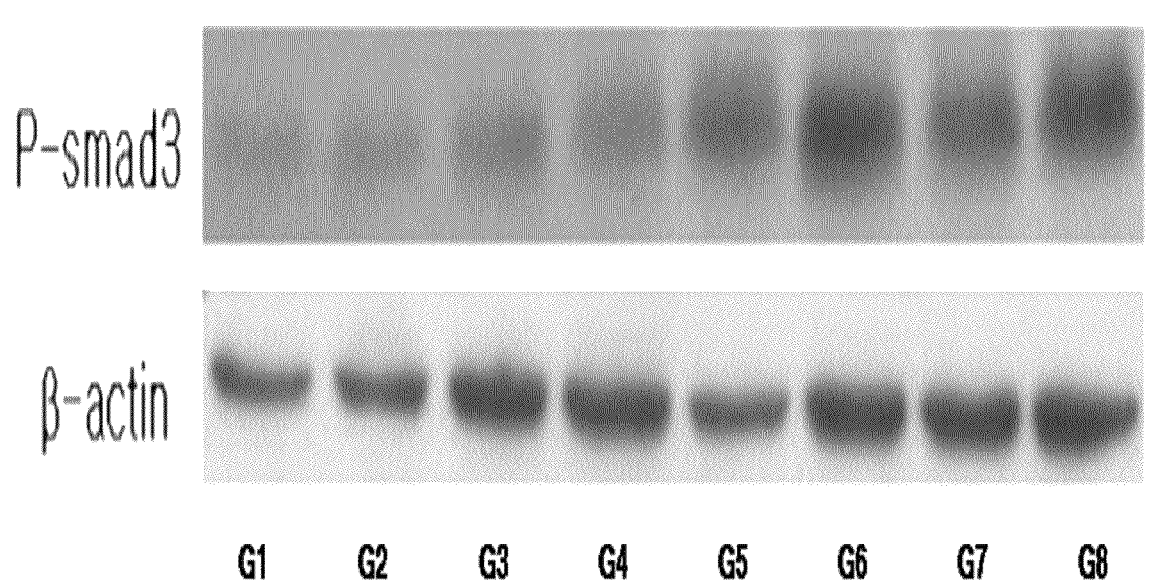
FIG. 9 is a set of photographs illustrating the result of immunoblotting with P-smad3 in the wild type and SMP30 knock out mice with acute liver injury.

The P-smad3 expression was higher in SMP30 knock-out mice (G5, G6, G7, G8) than in wild type mice (G1, G2, G3, G4). In particular, the highest P-smad3 expression was detected in SMP30 knock-out mouse group treated with $CCl_4$ alone (G6) but the expression was inhibited in both groups treated with vitamin C and arazyme (FIGS. 9 and 10).

Experimental Example 5

Detection of Smad3 in Liver Cells

<5-1> Immunohistochemical Observation of Smad3 Expression in Liver Cells

To investigate Smad3 expression in liver cells by immunohistochemical approach, experiments were performed by the same manner as described in Experimental Example <3-1> except that Smad3 (1:100, Santa Cruz Biotechnology Inc, USA) was used as primary antibody instead of SMP30.

As a result, there was no significant difference in Smad3 expressions between SMP30 knock-out mice and wild type mice. That is, Smad3 expressions were all consistent among experimental groups (FIGS. 11 and 12).

<5-2> Expression of Smad3 in Liver Cells Detected by Immunoblotting

To investigate Smad3 expression in liver cells by immunoblotting, experiments were performed by the same manner as described in Experimental Example <3-2> except that Smad3 (1:100, Santa Cruz Biotechnology Inc, USA) was used as primary antibody instead of SMP30 and anti-rabbit-HRP-antibody (1:1,000-1:2,000, Santa Cruz Biotechnology Inc, USA) was used as secondary antibody.

As a result, there was no significant difference in Smad3 expressions among all the experimental groups (FIG. 13). The Smad3 expression was consistent between wild type mouse groups (G1, G2, G3, G4) and SMP30 knock-out mouse groups (G5, G6, G7, G8).

Experimental Example 6

Immunohistochemical Observation of CYP2E1 Expression in Liver Cells

To investigate CYP2E1 expression in liver cells by immunohistochemical approach, experiments were performed by the same manner as described in Experimental Example <3-1> except that CYP2E1 (1:800 Santa Cruz Biotechnology Inc, USA) was used as primary antibody instead of SMP30.

As a result, CYP2E1 expression was strongly detected only in the group treated with arazyme and the expression levels of other groups were all similar (FIGS. 14 and 15). That is, CYP2E1 was highly expressed only in the groups treated with arazyme (G4, G8).

Experimental Example 7

Acute Cytotoxicity Test of Arazyme

The following experiments were performed to see if arazyme has acute toxicity in rats.

9-week old SPF (specific pathogen-free) Wistar line rats (Orient, Co., Seoul, Korea) were raised in an animal facility (4 groups, 4 rats per group) where temperature was regulated to 22±3° C., humidity was adjusted to 55±10% and light was also regulated to 12L/12D. The rats were quarantined and adapted for one week before being used. During the whole experiment period, the rats were raised in polycarbonate cages [240 W×390 L×175 H (mm)] by up to 5 per cage. Skin mark using an oil magic pen and individual identification card were used for distinguishment. Feed for laboratory animals (PMI Nutrition International, USA) was provided at any time after being sterilized. Tap water was provided using a water bottle at any time after being purified by a carbon filter.

Arazyme of the invention was dissolved in distilled water for injection at the concentrations of 0, 1250, 2500 and 5000 mg/kg, and 10 ml/kg of each arazyme solution was orally administered once to rats using zonde. After one week-adaptation, the rats were divided into four groups. Different concentrations of arazyme were administered to rats at 10 weeks, and general symptoms were checked. To evaluate toxicity of arazyme to organs, autopsy was performed 24 hours after the administration.

After oral-administration of arazyme to female rats, any symptom according to the administration was investigated and behavior, appearance and biological functions of rats were also observed to evaluate toxicity.

As a result, no specific symptoms in relation to motion, walking, temper and convulsions were observed. The appearance of the rat was also carefully observed and as a result no changes in hair coat, periocular region, ears, genitalia, limbs, and tail were detected. Biological functions such as respiration, salivation, feces and emesis were also observed and no abnormal symptoms were found. Autopsy was performed 24 hours after the administration of arazyme. The results of autopsy with naked eyes were also consistent with the above, indicating that the administration of arazyme did not cause any abnormal symptom or disorder in every organ. $LD_{50}$ of arazyme was estimated much greater than 5000 mg/kg. No pathological changes were observed in organs such as liver, heart, lung and spleen, by microscopic observation.

The Manufacturing Examples of the composition of the present invention are described hereinafter.

Manufacturing Example 1

Preparation of Pharmaceutical Formulation

<1-1> Preparation of Powders

| | |
|---|---|
| Arazyme | 2 g |
| Lactose | 1 g |

The above components are mixed and prepared in the form of powders, which filled air-tight bags.

<1-2> Preparation of Tablets

| | |
|---|---|
| Arazyme | 100 mg |
| Corn starch | 100 mg |
| Lactose | 100 mg |
| Magnesium stearate | 2 mg |

The above components are mixed and prepared in the form of tablet according to the conventional tablet preparation method.

<1-3> Preparation of Capsules

| | |
|---|---|
| Arazyme | 100 mg |
| Corn starch | 100 mg |
| Lactose | 100 mg |
| Magnesium stearate | 2 mg |

The above components are mixed and prepared in the form of capsule according to the conventional capsule preparation method.

<1-4> Preparation of Injectable Solutions

| | |
|---|---|
| Arazyme | 10 μg/ml |
| Diluted hydrochloric acid | to reach pH of 7.6 |
| Sodium chloride for injection | 1 ml at maximum |

Injectable solutions are prepared as follows. Arazyme is dissolved in a proper amount of injectable NaOH BP and pH of this solution is adjusted to 7.6 by using diluted hydrochloric acid BP. The injectable NaOH BP is used to regulate the volume of the solution. The well-mixed solution is filled in 5 ml type I glass ampoules. The glass mouth is sealed by being melted. The ampoules were sterilized by autoclave at 120° C. for at least 15 minutes.

Manufacturing Example 2

Preparation of Food

The present inventors have prepared food containing *Aranicola proteolyticus* culture solution or arazyme isolated therefrom as an active ingredient as follows.
<2-1> Preparation of Flour Food Health improving flour food was prepared by adding the *Aranicola proteolyticus* culture solution or arazyme isolated therefrom of the present invention by 0.1-10.0 weight part to wheat flour and then making the flour into bread, cakes, cookies, crackers and noodles.
<2-2> Preparation of Soups and Gravies The *Aranicola proteolyticus* culture solution or arazyme isolated therefrom of the present invention was added by 0.1-1.0 weight part to soups and gravies to prepare health improving soups and gravies of meat products and noodles.
<2-3> Preparation of Ground Beef The *Aranicola proteolyticus* culture solution or arazyme isolated therefrom of the present invention was added by 10 weight part to ground beef to prepare health improving ground beef.
<2-4> Preparation of Dairy Products The *Aranicola proteolyticus* culture solution or arazyme isolated therefrom of the present invention was added by 0.1-1.0 weight part to milk to prepare dairy products such as butter, ice cream, etc.
<2-5> Preparation of Sunsik Brown rice, barley, glutinous rice and coix (job's tear) were gelatinized by the conventional method, followed by drying. The dried mixture was distributed and pulverized, resulting in 60-mesh size grain powders.

Black bean, black sesame and perilla were steamed and dried by the conventional method. The dried mixture was distributed and pulverized, resulting in 60-mesh size grain powders.

The *Aranicola proteolyticus* culture solution or arazyme isolated therefrom of the present invention was vacuum-concentrated under reduced pressure using a vacuum concentrator, which was then spray-dried with a hot-air drier. The dried material was pulverized by a grinder, resulting in 60-mesh size grain powders.

The prepared grain, seeds, and dried powders of *Aranicola proteolyticus* culture solution or arazyme isolated therefrom were all mixed at the following ratio.

Grain (brown rice 30 weight part, coix 15 weight part, barley 20 weight part),
Seeds (perilla 7 weight part, black bean 8 weight part, black sesame 7 weight part),
Dried powders of *Aranicola proteolyticus* culture solution or arazyme isolated therefrom (1 weight part),
*Ganoderma lucidum* (0.5 weight part),
*Rehmannia glutinosa* (0.5 weight part)

Manufacturing Example 3

Preparation of Beverages

The present inventors have prepared beverages containing *Aranicola proteolyticus* culture solution or arazyme isolated therefrom as an active ingredient as follows.
<3-1> Preparation of Health Beverages Acid fructose (0.5%), oligosaccharide (2%), sugar (2%), salt (0.5%) and water (75%) were all mixed with the *Aranicola proteolyticus* culture solution or arazyme isolated therefrom evenly, followed by sterilization. The mixture was put in a small container such as a glass bottle or pat bottle, resulting in health beverages.
<3-2> Preparation of Vegetable Juice 0.5 g of *Aranicola proteolyticus* culture solution or arazyme isolated therefrom of the present invention was added to 1,000 ml of tomato or carrot juice to prepare health vegetable juice.
<3-3> Preparation of Fruit Juice 0.1 g of *Aranicola proteolyticus* culture solution or arazyme isolated therefrom of the present invention was added to 1,000 ml of apple or grape juice to produce health fruit juice.

INDUSTRIAL APPLICABILITY

As explained hereinbefore, the arazyme produced by *Aranicola proteolyticus* of the present invention inhibits necrosis of liver cells in injured liver, increases SMP30 expression, inhibits P-smad3 expression and protects liver by inhibiting liver injury around central vein. Therefore, arazyme of the invention can be effectively used as a pharmaceutical composition for the prevention of liver dysfunctions

SEQUENCE LIST TEXT

SEQ ID NO: 1 is the polypeptide sequence of *Aranicola proteolyticus*.
SEQ ID NO: 2 is the polynucleotide sequence of *Aranicola proteolyticus*.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for treating liver disease comprising administering an effective dose of a composition, comprising arazyme to a liver disease patient, wherein the arazyme comprises the amino acid sequence of SEQ ID NO: 1.

2. The method of claim 1, wherein the liver disease is selected from the group consisting of acute hepatitis, chronic hepatitis, fatty liver, liver cirrhosis, hepatic coma, alcoholic liver disease and hepatoma.

3. The method of claim 1, wherein the arazyme is isolated from an *Aranicola proteolyticus* culture solution.

4. The method of claim 3, wherein the *Aranicola proteolyticus* is *Aranicola proteolyticus* HY-3 as Korean Collection for Type Cultures (KCTC) Accession umber 0268BP.

5. The method of claim 1, wherein the arazyme inhibits apoptosis of a liver cell.

6. The method of claim 1, wherein the arazyme inhibits P-smad3 expression.

7. The method of claim 1, wherein the arazyme inhibits injury of a cell around a central vein region of the liver.

* * * * *